United States Patent [19]
Edwards

[11] Patent Number: 5,743,870
[45] Date of Patent: Apr. 28, 1998

[54] ABLATION APPARATUS AND SYSTEM FOR REMOVAL OF SOFT PALATE TISSUE

[75] Inventor: Stuart D. Edwards, Los Altos, Calif.

[73] Assignee: Somnus Medical Technologies, Inc., Sunnyvale, Calif.

[21] Appl. No.: 643,524

[22] Filed: May 6, 1996

Related U.S. Application Data

[63] Continuation-in-part of Ser. No. 516,781, Aug. 18, 1995, Pat. No. 5,674,191, which is a continuation-in-part of Ser. No. 239,658, May 9, 1994, Pat. No. 5,456,662.

[51] Int. Cl.$^6$ ............................................. A61B 17/39
[52] U.S. Cl. ................................................. 604/22
[58] Field of Search ............................ 604/22, 19–20, 604/164, 280, 53; 606/39, 32, 45; 607/96, 98, 134; 601/2

[56] References Cited

U.S. PATENT DOCUMENTS

| | | | |
|---|---|---|---|
| 3,901,241 | 8/1975 | Allen | 128/303.1 |
| 4,011,872 | 3/1977 | Komiya | 128/303.14 |
| 4,411,266 | 10/1983 | Cosman | 128/303.18 |
| 4,423,812 | 1/1984 | Sato | 206/387 |
| 4,532,924 | 8/1985 | Auth et al. | 128/303.17 |
| 4,565,200 | 1/1986 | Cosman | 128/642 |
| 4,901,737 | 2/1990 | Toone | 128/848 |
| 4,906,203 | 3/1990 | Margrave et al. | 439/188 |
| 4,907,589 | 3/1990 | Cosman | 606/34 |
| 4,947,842 | 8/1990 | Marchosky et al. | 128/401 |
| 4,966,597 | 10/1990 | Cosman | 606/50 |
| 4,976,711 | 12/1990 | Parins et al. | 606/48 |
| 5,046,512 | 9/1991 | Murchie | 128/848 |
| 5,057,107 | 10/1991 | Parins et al. | 606/48 |
| 5,078,717 | 1/1992 | Parins et al. | 606/48 |
| 5,083,565 | 1/1992 | Parins | 128/642 |
| 5,094,233 | 3/1992 | Brennan | 602/6 |
| 5,100,423 | 3/1992 | Fearnot | 606/159 |
| 5,122,137 | 6/1992 | Lennox | 606/40 |
| 5,125,928 | 6/1992 | Parins et al. | 606/48 |

(List continued on next page.)

FOREIGN PATENT DOCUMENTS

| | | |
|---|---|---|
| WO 92/10142 | 6/1992 | WIPO. |
| WO 93/08755 | 5/1993 | WIPO. |
| WO 96/29946 | 10/1996 | WIPO. |

OTHER PUBLICATIONS

Kaneko, et al., *Physical Laryngeal Pacemaker*, May 1985, Trans Am Soc Artif Intern Organs, vol. XXXI, pp. 293–296.

Mugica, et al., *Direct Diaphragm Stimulation*, Jan. 1987, PACE, vol. 10, pp. 252–256.

Mugica, et al., *Neurostimulation: An Overview*, Chapter 21, *Preliminary Test of a Muscular Diaphragm Pacing System on Human Patients*, 1985, pp. 263–279.

Nochomovitz, et al., *Electrical Activation of the Diaphragm*, Jun. 1988, Clinic in Chest Medicine, vol. 9, No. 2, pp. 349–358.

Prior, et al., *Treatment of Menorrhagia by Radiofrequency Heating*, 1991, Int. J. Hyperthermia, vol. 7, pp. 213–220.

Rice, et al., *Endoscopic Paranasal Sinus Surgery*, Chapters 5, *Functional Endoscopic Paranasal Sinus Surgery, The Technique of Messerklinger*, Raven Press, 1988, pp. 75–104.

Rice, et al., *Endoscopic Paranasal Sinus Surgery*, Chapters 6, *Total Endoscopic Sphenoethmoidectomy, The Technique of Wigand*, Raven Press, 1988, pp. 105–125.

Primary Examiner—Michael Buiz
Assistant Examiner—Manuel Mendez
Attorney, Agent, or Firm—Wilson Sonsini Goodrich & Rosati

[57] ABSTRACT

An ablation apparatus suitable for the ablation of soft palate tissue, including but not limited to the uvula, includes a cannula with a distal end and a proximal end and a lumen. A vacuum assisted retainer device is coupled to the cannula distal end. The vacuum retainer member includes a uvula receiving member configured to retain at least a portion of the uvula with the application of vacuum. An electromagnetic electrode is coupled to an electromagnetic energy source. A vacuum source is coupled to the uvula receiving member.

25 Claims, 9 Drawing Sheets

U.S. PATENT DOCUMENTS

| | | | |
|---|---|---|---|
| 5,190,541 | 3/1993 | Abele et al. | 606/46 |
| 5,197,963 | 3/1993 | Parins | 606/46 |
| 5,197,964 | 3/1993 | Parins | 606/48 |
| 5,215,103 | 6/1993 | Desai | 128/784 |
| 5,257,451 | 11/1993 | Edwards et al. | 29/825 |
| 5,275,162 | 1/1994 | Edwards et al. | 128/642 |
| 5,277,201 | 1/1994 | Stern | 607/98 |
| 5,281,217 | 1/1994 | Edwards et al. | 606/41 |
| 5,281,218 | 1/1994 | Imran | 606/41 |
| 5,290,286 | 3/1994 | Parins | 606/50 |
| 5,293,869 | 3/1994 | Edwards et al. | 128/642 |
| 5,309,910 | 5/1994 | Edwards et al. | 128/642 |
| 5,313,943 | 5/1994 | Houser et al. | 128/642 |
| 5,314,466 | 5/1994 | Stern et al. | 607/156 |
| 5,328,467 | 7/1994 | Edwards et al. | 604/95 |
| 5,348,554 | 9/1994 | Imran et al. | 606/41 |
| 5,363,861 | 11/1994 | Edwards et al. | 128/772 |
| 5,365,926 | 11/1994 | Desai | 128/642 |
| 5,366,490 | 11/1994 | Edwards et al. | 607/99 |
| 5,368,592 | 11/1994 | Stern et al. | 606/33 |
| 5,370,675 | 12/1994 | Edwards et al. | 607/101 |
| 5,370,678 | 12/1994 | Edwards et al. | 607/101 |
| 5,383,876 | 1/1995 | Nardella | 606/49 |
| 5,383,917 | 1/1995 | Desai | 607/702 |
| 5,385,544 | 1/1995 | Edwards et al. | 604/22 |
| 5,397,339 | 3/1995 | Desai | 687/116 |
| 5,398,683 | 3/1995 | Edwards et al. | 128/642 |
| 5,403,311 | 4/1995 | Abele et al. | 606/49 |
| 5,409,453 | 4/1995 | Lundquist et al. | 604/22 |
| 5,421,819 | 6/1995 | Edwards et al. | 604/22 |
| 5,423,808 | 6/1995 | Edwards et al. | 606/34 |
| 5,423,811 | 6/1995 | Imran et al. | 606/41 |
| 5,423,812 | 6/1995 | Ellman et al. | 606/45 |
| 5,433,739 | 7/1995 | Sluijter et al. | 607/99 |
| 5,435,805 | 7/1995 | Edwards et al. | 604/22 |
| 5,456,662 | 10/1995 | Edwards et al. | 604/22 |
| 5,456,682 | 10/1995 | Edwards et al. | 606/31 |
| 5,458,596 | 10/1995 | Lax et al. | 606/31 |
| 5,458,597 | 10/1995 | Edwards et al. | 606/41 |
| 5,470,308 | 11/1995 | Edwards et al. | 604/22 |
| 5,471,982 | 12/1995 | Edwards et al. | 128/642 |
| 5,472,441 | 12/1995 | Edwards et al. | 606/41 |
| 5,484,400 | 1/1996 | Edwards et al. | 604/22 |
| 5,486,161 | 1/1996 | Lax et al. | 604/22 |
| 5,505,728 | 4/1996 | Ellman et al. | 606/39 |
| 5,505,730 | 4/1996 | Edwards | 606/41 |
| 5,507,743 | 4/1996 | Edwards et al. | 606/41 |
| 5,509,419 | 4/1996 | Edwards et al. | 128/642 |
| 5,514,130 | 5/1996 | Baker | 606/41 |
| 5,514,131 | 5/1996 | Edwards et al. | 606/45 |
| 5,520,684 | 5/1996 | Imran | 606/41 |
| 5,531,676 | 7/1996 | Edwards et al. | 604/22 |
| 5,531,677 | 7/1996 | Lundquist et al. | 604/22 |
| 5,536,240 | 7/1996 | Edwards et al. | 604/22 |
| 5,536,267 | 7/1996 | Edwards et al. | 606/41 |
| 5,540,655 | 7/1996 | Edwards et al. | 604/22 |
| 5,542,915 | 8/1996 | Edwards et al. | 604/22 |
| 5,542,916 | 8/1996 | Hirsch et al. | 604/22 |
| 5,545,161 | 8/1996 | Imran | 606/41 |
| 5,545,171 | 8/1996 | Sharkey et al. | 606/148 |
| 5,545,193 | 8/1996 | Fleischman et al. | 607/99 |
| 5,549,108 | 8/1996 | Edwards et al. | 128/642 |
| 5,549,644 | 8/1996 | Lundquist et al. | 604/22 |
| 5,554,110 | 9/1996 | Edwards et al. | 604/22 |
| 5,556,377 | 9/1996 | Rosen et al. | 604/22 |
| 5,558,672 | 9/1996 | Edwards et al. | 606/41 |
| 5,558,673 | 9/1996 | Edwards et al. | 606/41 |

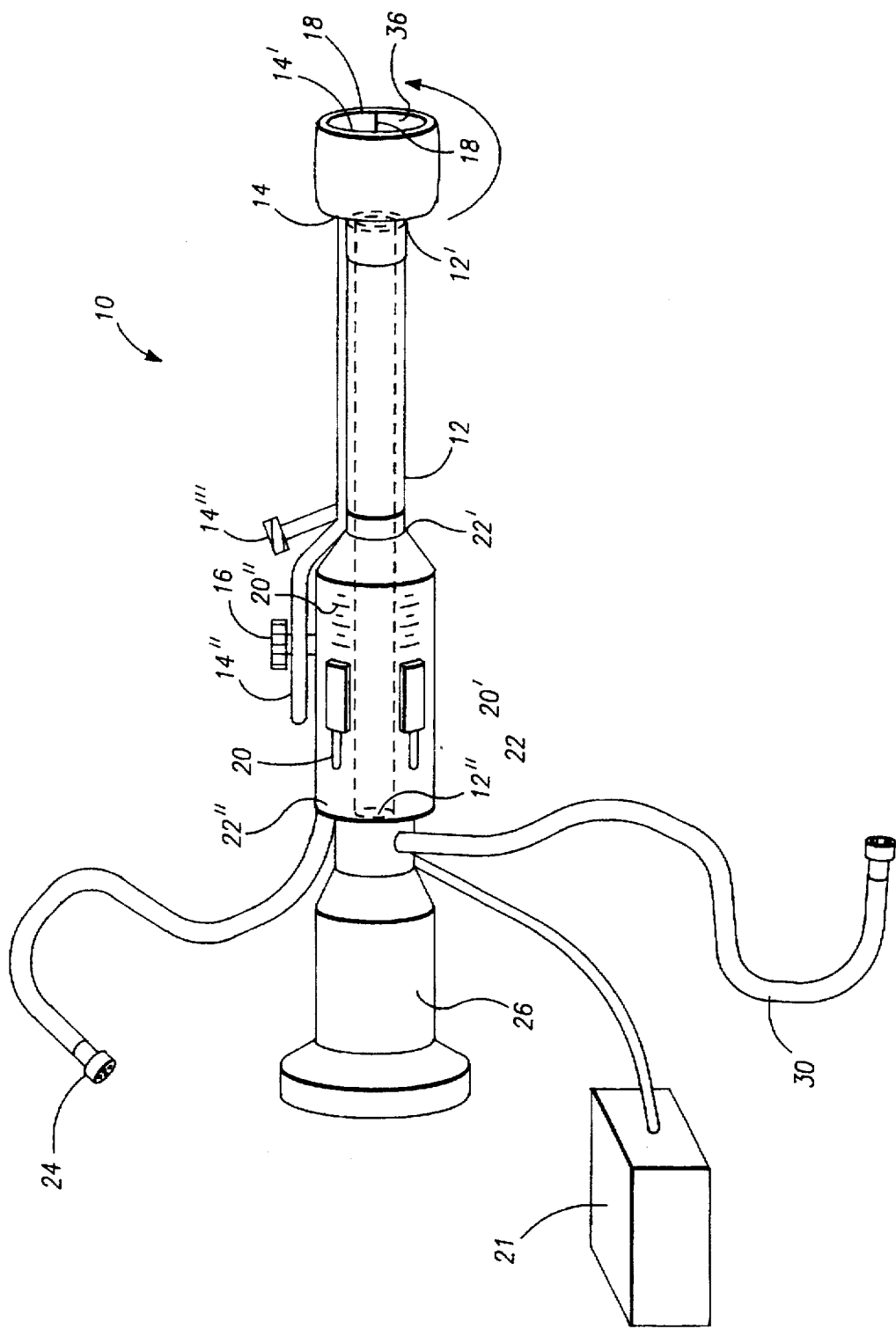
FIG. —1A

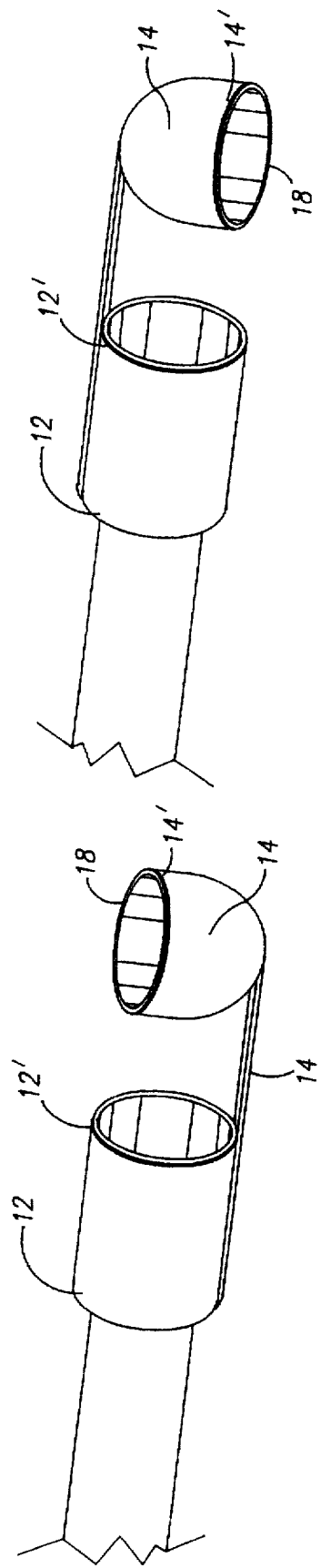

FIG.−6

ABLATION APPARATUS AND SYSTEM FOR REMOVAL OF SOFT PALATE TISSUE

CROSS REFERENCE TO RELATED APPLICATIONS

This application is a continuation-in-part application of U.S. Ser. No. 08/516,781, filed Aug. 18, 1995, now U.S. Pat. No. 5,674,191, which is a continuation-in-part of U.S. Ser. No. 08/239,658, filed May 9, 1994 (U.S. Pat. No. 5,456,662), having named inventors Stuart D. Edwards et al., and is incorporated herein by reference.

BACKGROUND OF THE INVENTION

1. Field of the Invention

This invention relates generally to an ablation apparatus for the removal of a variety of tissues, and more particularly to an RF, microwave, or laser fiber apparatus which ablates soft palate tissue including a portion of the uvula to treat snoring disorders.

2. Description of Related Art

Generally, there are two types of snoring. They are distinguished, depending on the localization of their origin. The first type of snoring, velar, is produced by the vibration of all of the structures of the soft palate including the velum, the interior and posterior arches of the tonsils and the uvula. Velar snoring results from a vibration of the soft palate created by the inspiratory flow of air, both nasal and oral, which makes the soft palate wave like a flag. The sound intensity of these vibrations is accentuated by the opening of the buccal cavity which acts as a sound box.

The second type, pharyngeal snoring, is a kind of rattle, including even horn whistling. It is caused by the partial obstruction of the oropharyngeal isthmus by the base of the tongue with, now and again, its total exclusion by the tongue base becoming jammed against the posterior wall of the pharynx. This results in a sensation of breathing, apnea, which constitutes the sleep apnea syndrome.

These two types of snoring may easily be combined in the same individual.

For some years there have been surgical techniques for correcting apnea. However, maxillary surgery to cure pharyngeal snoring requires major surgery, with the operation lasting several hours, and the uvula-palatopharnygoplasty procedure to correct velar snoring is not without draw backs. This explains the popularity of prosthesis and other preventive devices.

More recently, portions of the soft palate have been removed by laser ablation. If too much tissue is removed, severe consequences result. The degree of laser ablation is difficult to control and multiple treatments are usually required. Further, patients have a high degree of soreness in their throats for many weeks.

U.S. Pat. No. 4,423,812 discloses a loop electrode design characterized by a bare active wire portion suspended between wire supports on an electrode shaft. Tissue striping is effected with a bare wire, and the adjacent portions of the wire supports an electrode shaft that is made insulating to prevent accidental burns to the patient, allowing the physician to use these insulated parts to help position and guide the active wire portion during the surgical procedure. However, this requires that the physician shave off, during multiple visits, successive thin superficial layers of the obstructing tissues to avoid gross resection and its adverse affects.

U.S. Pat. No. 5,046,512 discloses a method for the treatment of snoring and apnea. The method regulates air flow to the user to an extent comparable to the volume of air which flows through the users nasal passages. An associated apparatus provides a device having a body portion sufficiently wide to separate the users teeth. It includes an air passage comparable in area to the area of the user's nasal passages.

The use of oral cavity appliances has been proposed frequently for the treatment of sleep disorders. It has been recognized that movement of the mandible forward relative to the maxilla can eliminate or reduce sleep apnea and snoring symptoms by causing the pharyngeal air passage to remain open. Several intra-oral dental appliances have been developed which the user wears at night to fix the mandible in an anterior protruded position. Such dental appliances essentially consist of acrylic or elastomeric bit blocks, similar to orthodontic retainers or athletic mouth guards, which are custom fitted to a user's upper and lower teeth. The device may be adjusted to vary the degree of anterior protrusion.

U.S. Pat. No. 4,901,737 discloses an intra-oral appliance while reducing snoring which repositions the mandible in an inferior, open, and anterior, protrusive, position as compared to the normally closed position of the jaw. Once the dentist or physician determines the operative snoring reduction position for a particular patient, an appropriate mold is taken for the maxillary dentition and of the mandibular dentition to form an appliance template. This device includes a pair of V-shaped spacer members formed from dental acrylic which extend between the maxillary and mandibular dentition to form a unitary mouthpiece.

While such dental appliances have proven effective in maintaining the mandible in a protruded position to improve airway patency, they often result in undesirable side effects. One of the most common side effects is aggravation of the tempromandibular joint and related jaw muscles and ligaments, especially in individuals who have a tendency to grind their teeth during sleep. Aggravation of the tempromandibular joint has be associated with a wide variety of physical ailments, including migraine headaches. Accordingly, many individuals suffering from sleep apnea and snoring disorders are not able to tolerate existing anti-snoring dental appliances for long periods of time.

It would be desirable to provide an ablation apparatus which eliminates the need for dental appliances for the treatment of snoring and sleep apnea disorders. It would also be desirable to provide a treatment device which is not an intra-oral dental appliance, and which can effectively and safely remove selected portions of the soft palate without providing the patient with undesirable side effects. Further, it would be desirable to provide a tissue ablation device which retains the targeted ablation tissue during the ablation process.

SUMMARY OF THE INVENTION

Accordingly, it is an object of the invention to provide an ablation device which is useful with a variety of tissues, and includes a retaining member to retain the tissue as it is ablated.

Another object of the present invention is to provide an ablation apparatus to treat snoring disorders.

A further object of the invention is to provide an ablation apparatus which can use a variety of electromagnetic energy sources to remove soft palate tissue and treat snoring disorders.

Yet a further object of the invention is to provide an ablation apparatus which can use a variety of electromagnetic energy sources, includes a retaining member to retain the tissue as it is ablated, and is suitable for ablating soft, hard, cartilage and mucosal tissues.

Yet another object of the invention is to provide an ablation apparatus to ablate sections of the uvula and other soft palette tissue.

Still another object of the invention is to provide an ablation apparatus including an anvil to position the uvula for ablation.

Another object of the invention is to provide an ablation apparatus including a vacuum retainer to position and retain the uvula and other soft palate tissue during ablation.

A further object of the invention is to provide an ablation apparatus which uses an RF energy source to ablate selected sections of the uvula and other soft palate tissue.

Yet another object of the invention is to provide an ablation system that includes a retaining member to retain an ablated tissue site, and the retaining member can be retracted so that an electromagnetic energy delivery source can be utilized without the retaining member.

These and other objects of the present invention are achieved in an ablation apparatus that includes a cannula with a distal end and a proximal end and a lumen. A vacuum assisted retainer device is coupled to the cannula distal end. The vacuum retainer member includes a uvula receiving member configured to retain at least a portion of the uvula with the application of vacuum. An electromagnetic electrode is coupled to an electromagnetic energy source. A vacuum source is coupled to the uvula receiving member.

In one embodiment of the invention, a method of ablating a portion of a uvula includes an ablation apparatus. The ablation apparatus includes a vacuum assisted retainer device coupled to the cannula distal end. The vacuum assisted retainer member consists of a uvula receiving member configured to retain at least a portion of the uvula with the application of a vacuum, and an electromagnetic energy electrode. At least a portion of a uvula is introduced in the uvula receiving member. A vacuum is applied to the uvula and retains the uvula in the uvula receiving member. Electromagnetic energy is applied from the electrode to the uvula in the uvula receiving member. An ablation lesion is formed within the uvula.

A variety of different tissues can be ablated, included but not limited to soft, hard, and mucosal tissue, as well as cartilage. The present invention is particularly suitable in ablating soft palate tissue for purposes of ablation and effecting a cure for snoring. The uvula can be retained by the retaining member as one or more electromagnetic energy delivery devices are advanced and retracted out of the uvula. Once the desired level of uvula ablation is achieved, the retaining member can be rotated and retracted in order to provide a straight shot for the electromagnetic energy delivery devices to be introduced into tissue that does not require retainment during ablation.

A variety of different electromagnetic energy sources can be used such as RF, microwave, laser, and the like. The electromagnetic delivery device can be an RF electrode (operated in mono-polar and bi-polar modes), a microwave antenna, an optical delivery fiber and the like.

When an RF electrode is used, an insulator can be positioned to surround the RF electrode and may be capable of slideable movement along an exterior of the electrode. This permits the length of an RF ablation surface to be varied. Further, the distal end of the anvil can be a ground pad electrode.

One more sensors can be incorporated at the cannula distal end and in the retaining member and its distal end. The cannula can have a hollow central lumen with one or more fluid distribution ports. A visualization apparatus can be positioned in the lumen. An eyepiece is coupled to the visualization apparatus at a proximal end of the cannula.

A flushing port can be formed in a cannula lumen. The flushing port is positioned near a distal end of the visualization apparatus in order to introduce a flushing medium past visualization apparatus distal end.

BRIEF DESCRIPTION OF THE FIGURES

FIG. 1(a) is a perspective view of the tissue ablation apparatus of the present invention, including a rotatable retaining member coupled to a vacuum source.

FIG. 1(b) is a perspective view of the top of the retaining member of FIG. 1(a).

FIG. 1(c) is a perspective view of a closed bottom of the retaining member of FIG. 1(a).

DETAILED DESCRIPTION

Figure 3:
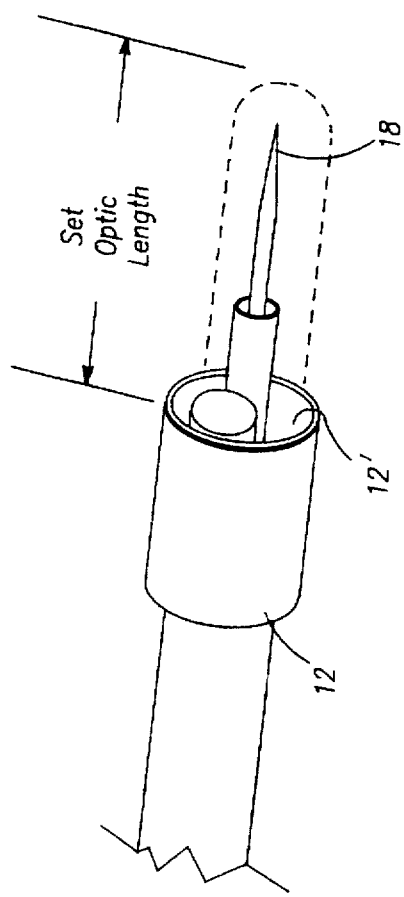
FIG. 3 is a perspective view of the distal end of the cannula and an electromagnetic energy delivery device extending beyond the cannula's distal end, establishing an optical length.

Referring now to FIG. 1(a) a soft tissue ablation apparatus 10 includes a cannula 12, a cannula distal end 12', a cannula proximal end 12" and a cannula lumen 12'". A retaining member 14 is coupled to cannula 12 and extends beyond distal end 12'. Retaining member 14 has a distal end 14' with a geometry that is adapted to surround an exterior of the uvula. A top of retaining member is open in order to receive the uvula. A bottom of the retaining member may be closed. Distal end 14' is adapted to capture, receive and retain a tissue ablation target during the ablation process.

A variety of different tissues can be ablated, included but not limited to soft, hard, and mucosal tissue, as well as cartilage. The present invention is particularly suitable in ablating soft palate tissue for purposes of ablation and effecting a cure for snoring. The uvula can be retained by retaining member 14 as one or more electromagnetic energy delivery devices deliver electromagnetic energy to the uvula. Once the desired level of uvula ablation is achieved, retaining member 14 is removed.

Retaining member 14 can be fastened with a fastener 16, including but not limited to a ground adjustment nut, and to the body of cannula 12. Alternatively, retaining member 14 can be integrally formed with cannula 12. A retaining member proximal end 14" can include a flushing port 14'" that is adapted to receive a flushing medium. Retaining member 14 can be rotatable relative to cannula 12.

Retaining member 14 can have a variety of different geometries such as an a cup-shaped member (FIG. 1(a)), with an open top (FIG. 1 (b)), and a closed bottom (FIG. 1(c)), and the like. Retaining member 14 physically retains and constrains the movement of a targeted ablation tissue before, during and after ablation One or more electromagnetic energy delivery devices 18 are positioned in lumen 12'", or in retaining member 14. Electromagnetic energy delivery devices 16 can be advanced out of retainer member 14 and introduced into the selected tissue target. Alternatively, electromagnetic energy delivery devices 16 can remain stationary in lumen 12'". Cannula 12 may be advanced and retracted in order to introduce and retract electromagnetic energy delivery devices 18 in and out of the soft palate tissue.

Electromagnetic energy delivery devices 18 can be of many varieties, including but not limited to an RF electrode 18 coupled to an RF energy source, a laser optical fiber 18 coupled to a laser source, a microwave antenna 18, and the like. Electromagnetic energy delivery devices 18 can have a sharpened distal end in order to pierce the targeted ablation tissue. A suitable RF electrode 18 is a needle electrode.

A deployment and retraction device 20 can be used to advance and retract electromagnetic energy delivery source 18 in and out of distal end 12' and the targeted ablation tissue. Deployment and retraction device 20 includes one or more actuators 20' that are mechanically coupled to electromagnetic energy delivery devices 18. Actuators 20' can be a variety of different knobs and the like that are hand activated. Actuators 20' can be positioned on an exterior surface of a handle 22 and moved axially, along gradation marks 20" to advance or retract. Gradation marks 20" provide an indication of, (i) the extension length of electromagnetic energy delivery devices 18 or (ii) the length of electromagnetic energy delivery devices 18 that is an ablation surface. Other movements of actuators 20' are suitable as long as they provide the appropriate advancement and retraction of electromagnetic energy delivery devices 18.

A vacuum source 21 extends to retainer member 14. Retainer member 14 provides for the retention of the uvula upon the application of vacuum. The soft palate tissue, including but not limited to the uvula, is positioned within an interior of retainer member 14. Vacuum is applied and the soft palate tissue is retained. With the soft palate tissue retained, electromagnetic energy delivery device is introduced into the soft palate tissue. Alternatively, upon application of vacuum, the electromagnetic energy delivery device can include a geometry that at least partially surrounds an exterior of the soft palate tissue. Electromagnetic energy is then applied to an exterior of the soft palate.

A handle 22 includes a distal end 22' and a proximal end 22". Cannula 12 can be at least partially positioned in handle 22, or at least coupled to distal end 22'. In certain instances, cannula 12 also extends past proximal end 22". A multi-plug 24 extends from proximal end 22", out of an adapter 26 coupled to proximal end 22" or out of proximal end 12". Multi-plug 24 receives a variety of different cables or lines that are coupled to sensors 36, electromagnetic energy delivery devices 18 and other devices. For example, multi-plug 24 can receive lines coupled to, (i) sensors 36, (ii) an RF electrode 18, (iii) a laser optical fiber 18 or (iv) a microwave antenna 18. Further, a light source cable 30 can be coupled to handle 22, adaptor 26 or distal end 12'.

Electromagnetic energy delivery device 18 can remain in a fixed position relative to cannula 12. In this instance, cannula 12 itself is advanced and retracted from distal end 22' in order to introduce and retract electromagnetic energy delivery devices 18 in and out of the target ablation tissue.

An eyepiece can be coupled at a proximal end of soft tissue ablation apparatus, e.g., to proximal end 22", proximal end 12' or adaptor 26.

Figure 2:
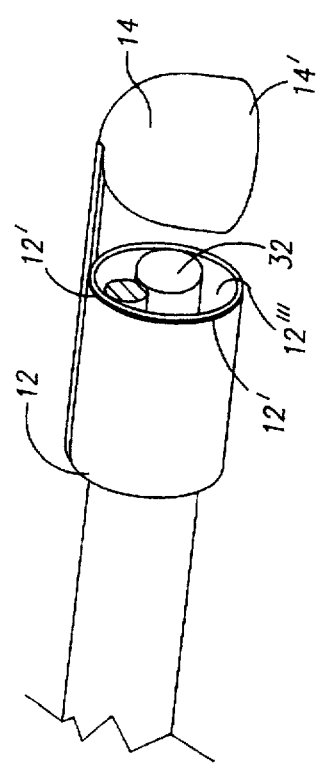
FIG. 2 is a perspective view of the cannula with a needle electrode or antenna and the retaining member of FIG. 1(a).

FIG. 2 more fully illustrates distal end 12'. A visualization apparatus 32 is positioned in lumen 12'" and can be positioned adjacent to electromagnetic energy delivery device 18. As shown, visualization apparatus extends to distal end 12'. It will be appreciated that visualization apparatus can be slideably positioned in lumen 12'" and advance beyond distal end 12'. Further, visualization apparatus 32 can be retained in lumen 12'" and cannula 12 can itself be advanced causing visualization apparatus 32 to move. Visualization apparatus 32 includes optics, an illumination source such as a plurality of optical fibers, and the like, as is well known to those skilled in the art.

As shown in FIG. 3, when electromagnetic energy delivery device 18 is advanced from distal end 12' an optical path length is established. It is within this optical path length that visualization is established. After the uvula has first received a topical anesthetic, electromagnetic energy delivery device 18 is introduced into the uvula. A suitable topical anesthetic includes but is not limited to lidocaine and can be administered out of an aperture formed in retaining member 14, cannula 12, and the like. The ablation of the targeted tissue is under full visualization. Distal end 14' holds the uvula in place as the lidocaine is sprayed and electromagnetic energy delivery device 18 introduced.

Figure 4:
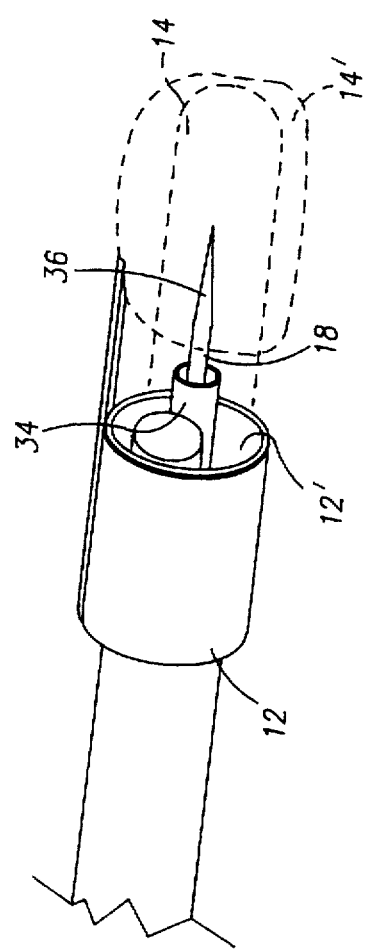
FIG. 4 is a perspective view of a distal end of the cannula, with a thermal sensor and the retaining member of FIG. 1(a).

Referring now to FIG. 4, an insulation layer 34 is positioned around the exterior of electromagnetic energy delivery device 18 when it is an RF electrode. A slideable insulation layer 34 surrounds electrode 12. In one embodiment insulation 34 can comprise a polyimide material, a thermal sensor 36 positioned on top of the polyimide insulation, and a0.002 inch shrink wrap. The polyimide insulating layer is semi-rigid. Sensor 36 can lay down substantially the entire length of the polyimide.

Figure 5:
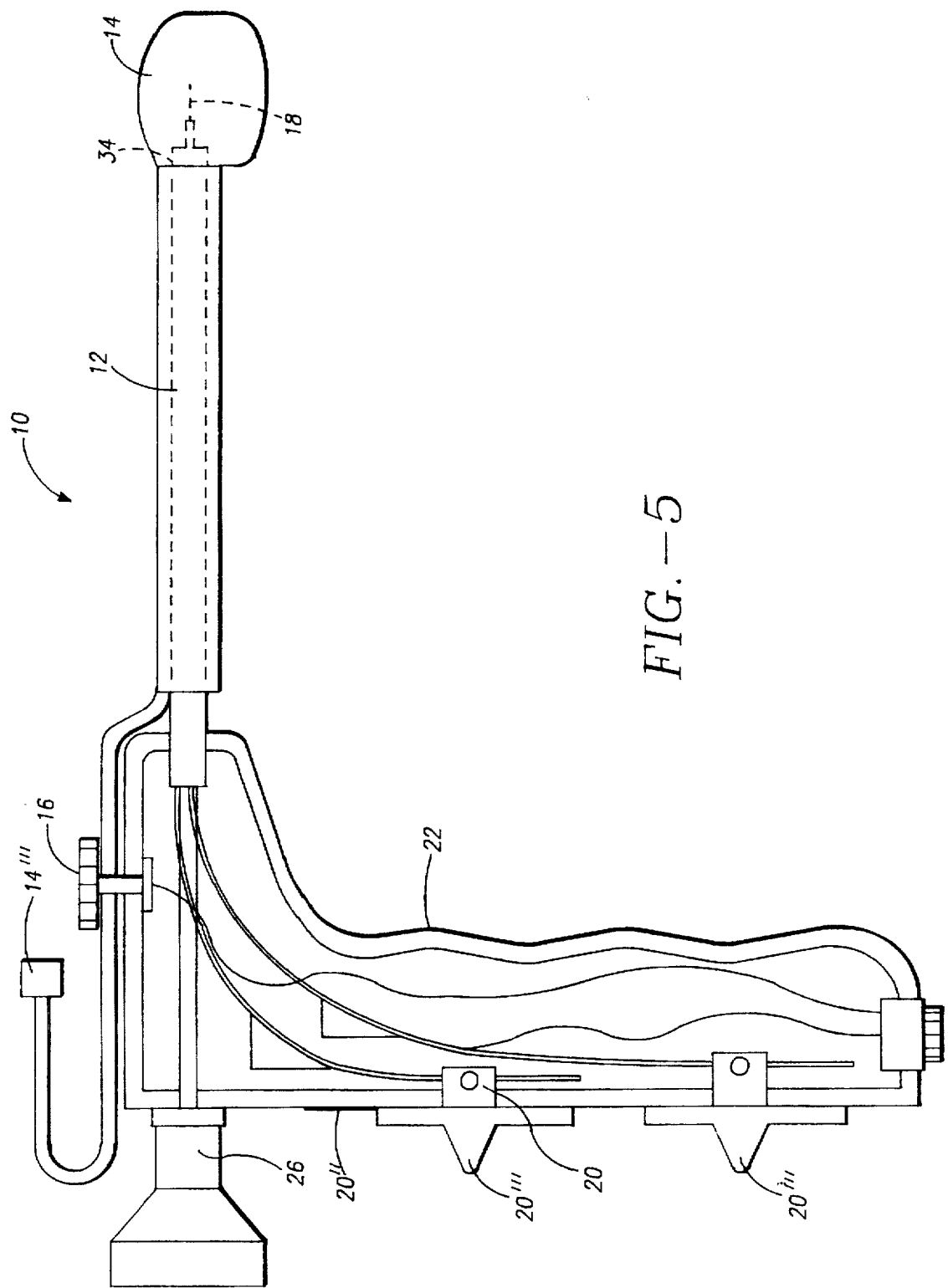
FIG. 5 is a perspective view of the apparatus of the present invention with a handle.

FIG. 5 illustrates the mechanical attachment of deployment apparatus 20 with electromagnetic energy delivery device (RF electrode 18'). Further, handle 22 is more readily adapted to be held as a trigger. An actuator 20'" is positioned at the exterior of handle 22 and is advancement back and forth along gradation marks 20" to adjust the length of insulation layer 34 that covers RF electrode 18'. This provides a variable area of RF electrode 18' that serves as the RF electromagnetic energy ablation surface.

Figure 6:
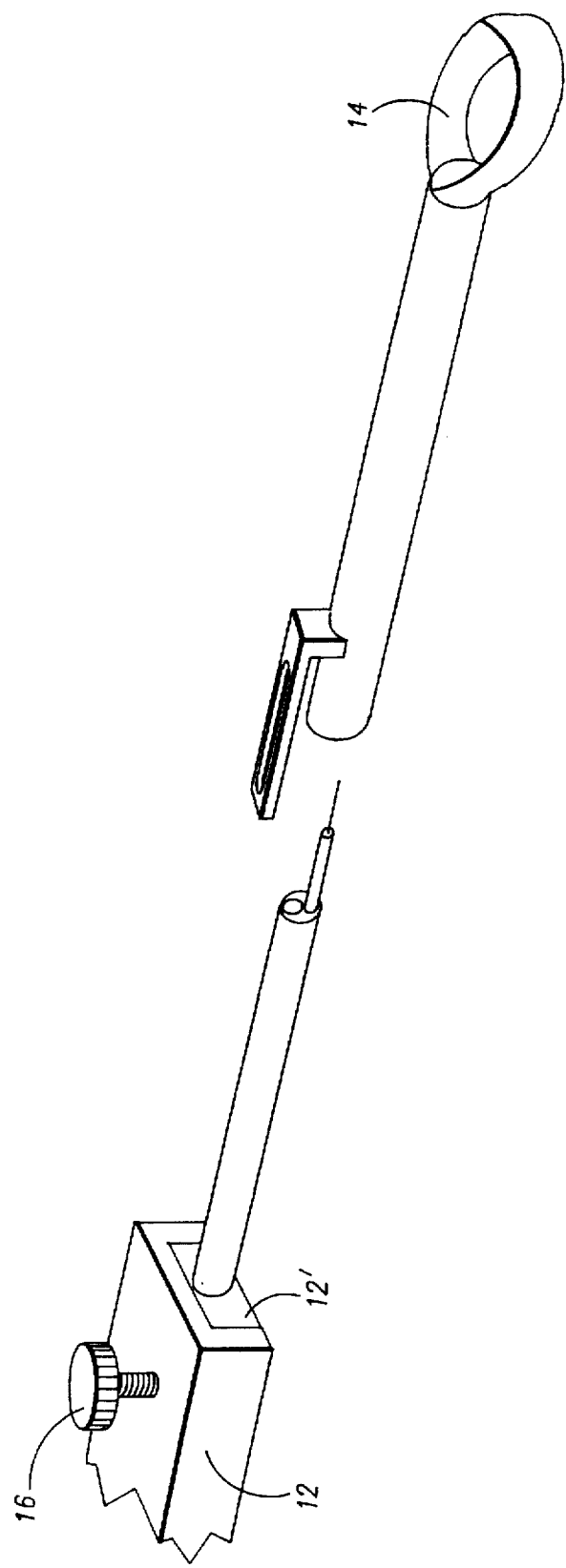
FIG. 6 is an exploded view of the retaining member of FIG. 1(a) and the cannula.

Referring now to FIG. 6, retaining member 14 can be removed completely away from cannula 12. This permits soft tissue ablation apparatus 10 to be used in a variety of soft tissue applications besides the uvula, including but not limited to other soft palate structures, the turbinates and the like. Alternatively, retaining member 14 is slightly rotated and withdrawn past distal end 12'.

Figure 7:
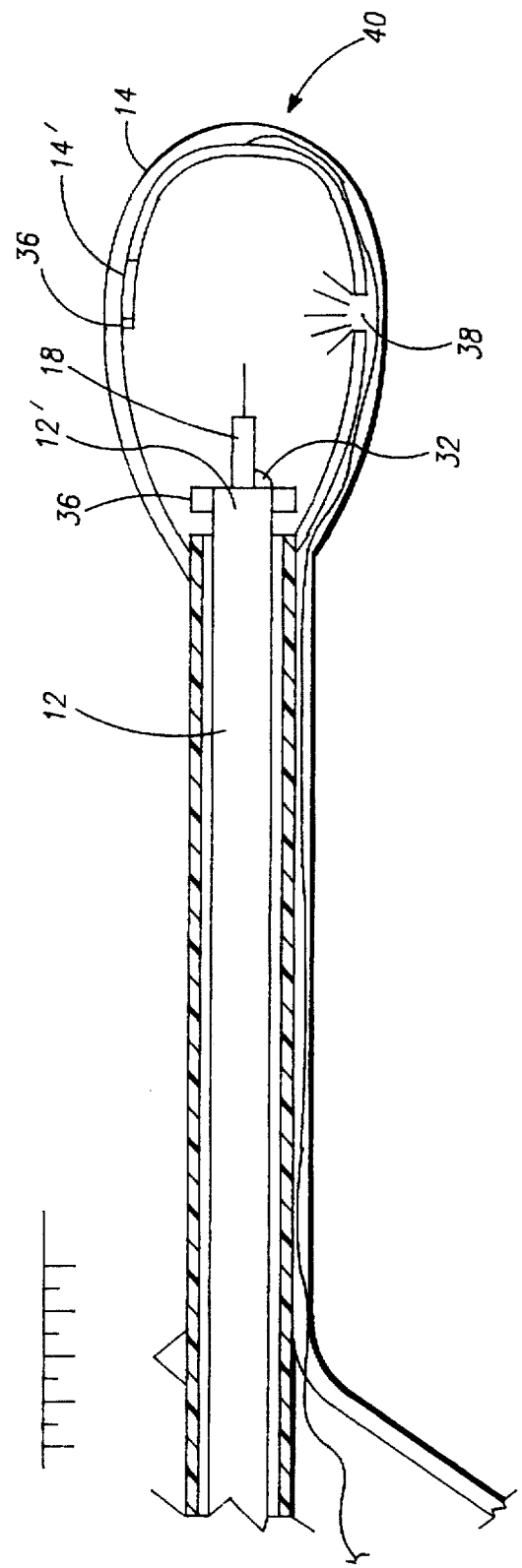
FIG. 7 is a perspective view of a flushing port or optic port associated with the retaining member of FIG. 1(a).

Referring now to FIG. 7, a flushing aperture 38 is included in retaining member 14 to spray a flushing medium across visualization apparatus 32, particularly the optics, in order to clean visualization apparatus 32. This provides a clean view of the site. Additionally, a flushing aperture can be included in distal end 12'. One or more thermal sensors 36 can be positioned at distal end 14', at distal end 12', at a distal end of electromagnetic energy delivery device 18, as well as other positions to measure temperature and determine when sufficient electromagnetic energy has been applied to the soft tissue.

Sensors 36 provide temperature measurement and monitoring of the target to be ablated and permit a desired level of ablation to be achieved without necrosing too much tissue. This reduces damage to surrounding tissue. By monitoring the temperature at a central point within the interior of the selected mass, a determination can be made when ablation is complete. If at any time sensor 36 determines that a desired ablation temperature is exceeded, then an appropriate feedback signal is received at the electromagnetic energy source which then regulates the amount of power delivered to electromagnetic energy delivery device 18.

By monitoring temperature, power delivery can be accelerated to a predetermined or desired level. In the case of RF energy, impedance is used to monitor voltage and current. The readings of sensors 36 regulate voltage and current that is delivered to the tissue site. The output for these sensors 36 is used by a controller, described further in this disclosure, to control the delivery of electromagnetic energy to the tissue site. Resources, which can be hardware and/or software, are connected with the thermal sensors 36, the power source and to electromagnetic energy delivery device 18. The resources provide an output for delivering and maintaining a selected electromagnetic energy delivery device 18. Further the resources provide an output that maintains a selected RF energy for a selected length of time. If RF energy is used, the resources are associated with sensors 36, a ground pad electrode (if included) as well as the RF power source for maintaining a selected power at RF electrode 18 independent of changes in voltage or current. Sensors 36 are of conventional design, including but not limited to thermistors, thermocouple, resistive wires, and the like.

Suitable thermal sensors 36 include a T type thermocouple with copper constantene, J type, E type, K type, thermistors, fiber optics, resistive wires, thermocouple IR detectors, and the like. It will be appreciated that sensors 36 need not be thermal sensors.

The following discussion pertains particularly to the use of an RF energy source and RF electrode 18. It will be appreciated that devices similar to those associated with RF electrode 18 can be utilized with laser optical fibers, microwave devices and the like.

Figure 8:
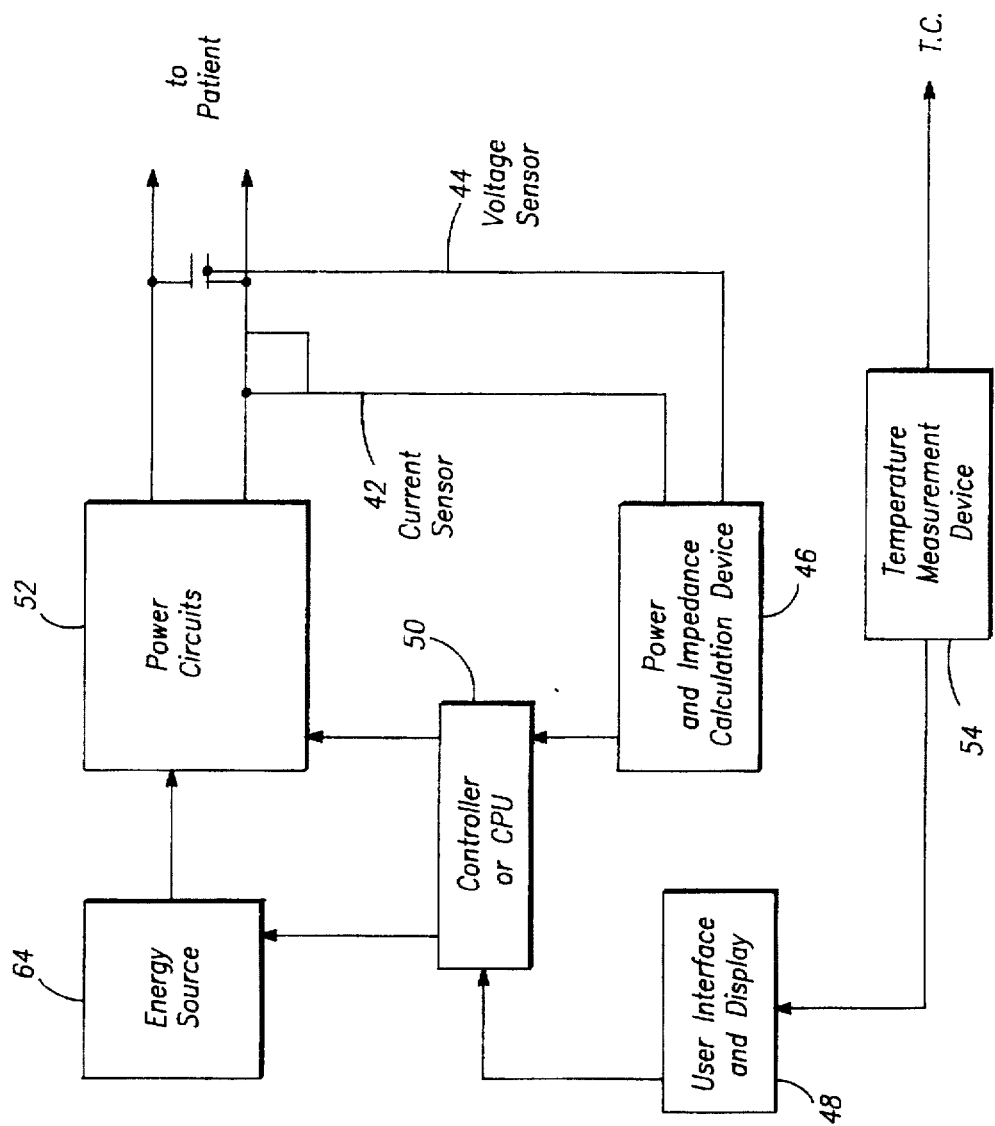
FIG. 8 is a block diagram illustrating the inclusion of a controller, power source and other electronic components of the present invention.

Referring now to FIG. 8 current delivered through RF electrode 18 is measured by current sensor 42. Voltage is measured by voltage sensor 44. Impedance and power are then calculated at power and impedance calculation device 46. These values can then be displayed at user interface and display 48. Signals representative of power and impedance values are received by controller 50.

A control signal is generated by controller 50 that is proportional to the difference between an actual measured value, and a desired value. The control signal is used by power circuits 52 to adjust the power output in an appropriate amount in order to maintain the desired power delivered at the respective RF electrode 18.

In a similar manner, temperatures detected at the thermal sensors 36 provide feedback for maintaining a selected power. The actual temperatures are measured at temperature measurement device 54, and the temperatures are displayed at user interface and display 48. A control signal is generated by controller 50 that is proportional to the difference between an actual measured temperature, and a desired temperature. The control signal is used by power circuits 52 to adjust the power output in an appropriate amount in order to maintain the desired temperature delivered at the respective sensor.

Controller 50 can be a digital or analog controller, or a computer with software. When controller 50 is a computer it can include a CPU coupled through a system bus. On this system can be a keyboard, a disk drive, or other non-volatile memory systems, a display, and other peripherals, as are known in the art. Also coupled to the bus are a program memory and a data memory.

User interface and display 48 includes operator controls and a display. Controller 50 can be coupled to imaging systems, including but not limited to ultrasound, CT scanners and the like.

Current and voltage are used to calculate impedance. Diagnostics can be performed optically, with ultrasound, CT scanning, and the like. Diagnostics are performed either before, during and after treatment.

The output of current sensor 42 and voltage sensor 44 are used by controller 50 to maintain the selected power level at RF electrode 18. The amount of RF energy delivered controls the amount of power. A profile of power delivered can be incorporated in controller 50, and a pre-set amount of electromagnetic energy to be delivered can also be profiled.

Circuitry, software and feedback to controller 50 result in process control, and the maintenance of the selected power that is independent of changes in voltage or current, and are used to change, (i) the selected power, including RF, microwave, laser and the like, (ii) the duty cycle (on-off and wattage), (iii) bipolar electromagnetic energy delivery and (iv) fluid delivery, including flow rate and pressure. These process variables are controlled and varied, while maintaining the desired delivery of power independent of changes in voltage or current, based on temperatures monitored at the thermal sensors 36.

Figure 9:
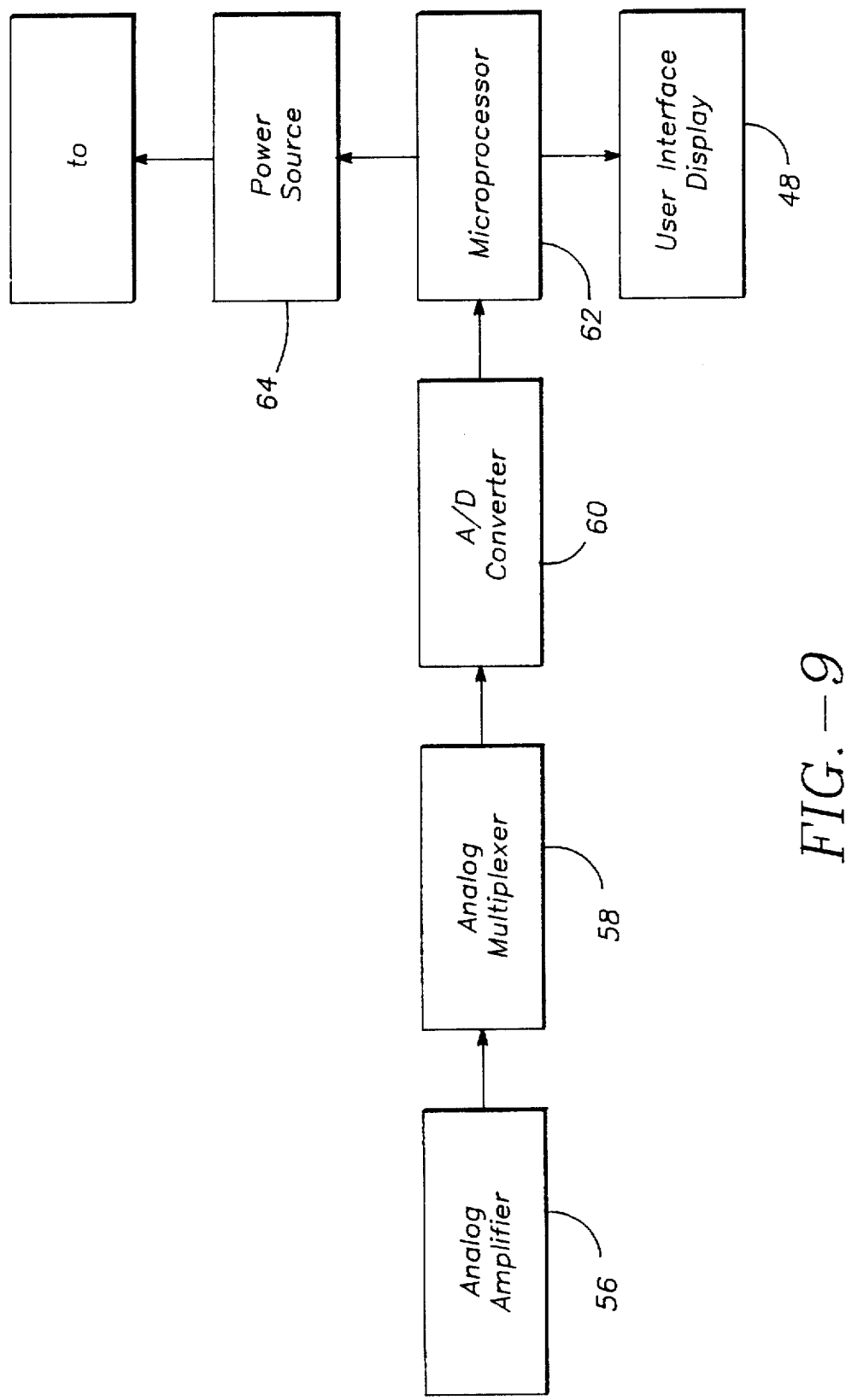
FIG. 9 is a block diagram illustrating an analog amplifier, analog multiplexer and microprocessor used with the present invention.

Referring now to FIG. 9, current sensor 42 and voltage sensor 44 are connected to the input of an analog amplifier 56. Analog amplifier 56 can be a conventional differential amplifier circuit for use with the thermal sensors 36. The output of analog amplifier 56 is sequentially connected by an analog multiplexer 58 to the input of A/D converter 60. The output of analog amplifier 56 is a voltage which represents the respective sensed temperatures. Digitized amplifier output voltages are supplied by A/D converter 60 to a microprocessor 62. Microprocessor 62 may be a model no. 68HC11 available from Motorola. However, it will be appreciated that any suitable microprocessor or general purpose digital or analog computer can be used to calculate impedance or temperature.

Microprocessor 62 sequentially receives and stores digital representations of impedance and temperature. Each digital value received by microprocessor 62 corresponds to different temperatures and impedances.

Calculated power and impedance values can be indicated on user interface and display 48. Alternatively, or in addition to the numerical indication of power or impedance, calculated impedance and power values can be compared by microprocessor 62 with power and impedance limits. When the values exceed predetermined power or impedance values, a warning can be given on user interface and display 48, and additionally, the delivery of RF energy can be reduced, modified or interrupted. A control signal from microprocessor 62 can modify the power level supplied by power source 64.

An imaging system can be used to first define the volume of the targeted ablation tissue that will be ablated. Suitable imaging systems include but are not limited to, ultrasound, CT scanning, X-ray film, X-ray fluoroscope, magnetic resonance imaging, electromagnetic imaging and the like. The use of such devices to define a volume of a tissue mass or a tumor is well know to those skilled in the art.

Specifically with ultrasound, an ultrasound transducer transmits ultrasound energy into a region of interest in a patient's body. The ultrasound energy is reflected by different organs and different tissue types. Reflected energy is sensed by the transducer, mad the resulting electrical signal is processed to provide an image of the region of interest. In this way, the volume to be ablated is ascertained.

The foregoing description of a preferred embodiment of the invention has been presented for purposes of illustration and description. It is not intended to be exhaustive or to limit the invention to the precise forms disclosed. Obviously, many modifications and variations will be apparent to practitioners skilled in this art. It is intended that the scope of the invention be defined by the following claims and their equivalents.

What is claimed is:

1. An ablation apparatus, comprising:
   a handpiece including a distal portion and a proximal portion;
   an ablation energy delivery device configured to extend from a distal portion of the handpiece into an interior of a selected oral cavity anatomical structure and further configured to be coupled to an energy source, the ablation energy delivery device including a and
   a vacuum assisted retainer device coupled to the handpiece distal portion, wherein the vacuum assisted retainer device is configured to be coupled with a vacuum source, and apply a vacuum force to the exterior surface of the oral cavity anatomical structure.

2. The apparatus of claim 1, wherein the electromagnetic electrode is at least partially positioned in an interior of the uvula receiving member.

3. The apparatus of claim 1, wherein the electromagnetic electrode is coupled to the distal end of the cannula.

4. The apparatus of claim 3, wherein the ablation energy delivery device advancement device is coupled to the handpiece.

5. The apparatus of claim 1, wherein the ablation energy delivery device distal end is configured to be positionable within an interior section of the oral cavity anatomical structure tissue.

6. The apparatus of claim 1, wherein the ablation energy delivery device distal portion is configured to be substantially positionable within a central interior section of the oral cavity anatomical structure.

7. The apparatus of claim 1, wherein an electromagnetic electrode has a geometry configured to surround at least a portion of an exterior of the uvula.

8. The apparatus of claim 1, wherein the electromagnetic electrode includes a thermal sensor.

9. The apparatus of claim 7, wherein at least a portion of the ablation energy delivery device is configured to form at one linear section which extends in a lateral direction relative to the longitudinal axis of the handpiece.

10. The apparatus of claim 1, wherein the uvula receiving member includes a thermal sensor.

11. The apparatus of claim 1, wherein the uvula receiving member includes a thermal sensor positioned on an exterior surface of the uvula receiving member.

12. The apparatus of claim 1, wherein the oral cavity soft anatomical structure is the uvula.

13. The apparatus of claim 12, further comprising:
    an insulator in at least a partially surrounding relationship to the RF electrode.

14. The apparatus of claim 1, wherein the uvula receiving member includes a fluid distribution port.

15. The apparatus of claim 1, further comprising:
    a visualization apparatus including a distal end extending to the uvula receiving member.

16. The apparatus of claim 15, further comprising:
    an eyepiece coupled to the visualization apparatus and positioned at the proximal end of the cannula.

17. A method of ablating a portion of a uvula, comprising:
    providing an ablation apparatus including a cannula, a vacuum assisted retainer device coupled to the cannula distal end, the retainer member including a uvula receiving member configured to retain at least a portion of the uvula with the application of a vacuum, and an electromagnetic electrode;
    introducing at least a portion of a uvula in the uvula receiving member;
    applying a vacuum to the uvula and retain the uvula in the uvula receiving member
    applying electromagnetic energy from the electrode to the uvula in the uvula receiving member; and
    forming an ablation lesion within the uvula.

18. The method of claim 17, wherein the electrode is an RF electrode coupled to an RF energy source.

19. The method of claim 18, wherein the RF ablation electrode is a needle electrode.

20. The method of claim 18, wherein the RF ablation apparatus operates in a bipolar mode.

21. The method of claim 18, wherein the RF ablation apparatus operates in a monopolar mode.

22. The apparatus of claim 1, wherein the energy source is a microwave source providing energy from 915 MHz to 2.45 GHz and the ablation energy delivery device is a microwave antenna.

23. The apparatus of claim 1, wherein the energy source is an ultrasound source and the ablation energy delivery device is an ultrasound emitter.

24. The apparatus of claim 10, wherein the ultrasound source produces energy in the range of 300 KHZ to 3 GHz.

25. The apparatus of claim 1, wherein the energy source is a microwave source.

* * * * *